United States Patent [19] [11] 3,950,104
Munk [45] Apr. 13, 1976

[54] REFRACTIVE INDEX AND FLOW RATE DETECTOR AND METHOD

[75] Inventor: Miner N. Munk, Walnut Creek, Calif.

[73] Assignee: Varian Associates, Palo Alto, Calif.

[22] Filed: July 22, 1974

[21] Appl. No.: 490,593

[52] U.S. Cl. .................. 356/128; 356/246; 73/204
[51] Int. Cl.² .. G01N 21/46; G01N 1/10; G01F 1/68
[58] Field of Search ........... 356/128, 129, 130, 134, 356/246; 73/204

[56] References Cited
UNITED STATES PATENTS
2,362,235   11/1944   Barnes .............................. 356/129
2,968,209   1/1961   Aulin ................................ 356/129

Primary Examiner—John K. Corbin
Assistant Examiner—Conrad Clark
Attorney, Agent, or Firm—Stanley Z. Cole; Gerald M. Fisher; John J. Morrissey

[57] ABSTRACT

Apparatus and method for detecting the refractive index and rate of fluid flowing through an elongated flow cell, having applications in liquid chromatography. The cell may be of circular cross section and has an input window in one end, an exit window in the other, and a longitudinal side wall. A light source directs divergent light through the entrance window, longitudinally through the cell, to pass through the exit window and be sensed by a photoelectric detector outside the exit window. In a first embodiment, heat transmission apparatus connected to the cell establishes a constant temperature gradient in the cell. This temperature gradient, preferably, has a component perpendicular to the longitudinal dimension of the cell and extending toward the center of the cell. This causes the density of the fluid in the cell to vary as an increasing function of its distance from the walls. The index of refraction of the fluid thus, in this embodiment, increases with distance from the cell walls. This causes the divergent light to be bent away from the cell walls, and toward the center of the cell. The degree of this bending, and hence the fraction of light entering the entrance window which passes through the exit window, increases with the refractive index of the fluid. By appropriate selection of the cell dimensions, of the value of the temperature gradient and of a substantially constant flow rate of the fluid, the bending of the light passing through the cell may be governed such that the fraction of entering light which exits from the cell is a highly dependent function of variations in the refractive index of the fluid in the flow cell. In another embodiment, a fluid having a known refractive index value has its flow rate determined by measuring the absorbance of a beam of light passed therethrough after establishing a temperature gradient in the fluid such that the degree of light bending is influenced by the flow rate.

27 Claims, 10 Drawing Figures

FIG.5b

REFRACTIVE INDEX AND FLOW RATE DETECTOR AND METHOD

BACKGROUND OF THE INVENTION

1. Field of the Invention

This invention relates to an apparatus and method for detecting the refractive index and flow rate of a fluid, and particularly to such apparatus and method for use as detectors in liquid chromatography.

2. The Prior Art

Liquid chromatography pertains to a particular variety of equipment and techniques for analyzing the components of an unknown sample of liquid material.

Liquid chromatography is a process wherein a sample having unknown components is forced to migrate through an elongated "column". The column contains a material held statically inside it, called a "stationary phase". The stationary phase is chosen for its ability to selectively retain the various potential components of the sample with which it comes in contact with differing degrees of tenacity. The sample is forced to migrate through the column by injecting it into a solvent upstream of the column and subsequently pumping the solvent and dissolved sample through the column.

When the dissolved sample is forced through the column, each of its components migrates through the column in a particular time related pattern, which pattern is a function of the degree of the tendency of the stationary phase to retain that component.

Some properties of the column effluent, following the pumping of the solvent and dissolved sample through the column, are affected by the concentration of sample in the emergent fluid. One of the properties which is typically so affected is the refractive index of the effluent. By detecting variations in such properties of the column effluent, and by plotting these variations against time, certain information can be derived as to the nature and amount of the components in the sample.

For example, for predetermined column conditions and flow rate, it may be known that a particular hypothetical component, if present in the sample, will reach a maximum concentration in the column effluent at a specific time following introduction of the sample to the column. This time is known as the "retention time" of the component. This phenomenon occurs because of the existence of a particular degree of retention of that component by the stationary phase. By measuring a property of the effluent known to be affected by the hypothetical component, and observing whether a maximum occurs at the "retention time" for that component, the presence of the component can be verified or negated.

Conditions of the effluent affect precise determination of some hypothetical components, such as effluent flow rate affecting the retention time of the component. Therefore the flow rate is desirably known even in systems inconvenient for flow rate measurement.

It is evident that in liquid chromatography there exists a necessity for accurately detecting and measuring, on a continuous basis, properties of the liquid emerging from the column, such as refractive index. It is further evident that a necessity exists for determining effluent conditions in liquid chromatography systems such as fluid flow rate, notwithstanding inconvenience of measurement.

Several types of apparatus exist for detecting changes in the index of refraction of the column effluent. One (called "deflective" type) involves passing the column effluent through an elongated flow cell having a triangular cross-section, the hypotenuse of which triangle forms an interface with that of a second triangular cross-sectional chamber. The second chamber contains a reference fluid having a known index of refraction. A mirror is placed parallel to one of the legs of the second chamber at a distance therefrom. A light beam is then directed through the two chambers, and across the interface, at which point it is bent, and transmitted on to the mirror at an angle of incidence dependent upon the difference between the indices of refraction of the column effluent and the reference fluid. The light beam is reflected from the mirror and returns back across the interface, being bent additionally as it crosses the interface to an angle even further removed from the angle at which the incoming light beam was incident on the interface for the first time. The degree of deflection of the light beam is measured, and is a function of the difference between the respective indices of refraction of the column effluent and the reference fluid.

Another type of refractive index detector employs two beams of light which originate from a common region of a tungsten filament lamp. The two parallel beams of light pass through a glass prism, and are partially transmitted through two glass-liquid interfaces. One interface is the boundary of the detection flow cell and the prism, and the other interface is the boundary of a reference cell with the prism. The two transmitted beams of light are then scattered from a finely ground stainless steel back plate, and a part of the scattered light from each of the beams is transmitted back through its respective cell, the glass prism and on to two halves of a photoconductive sensing cell.

The ratio of the amount of light transmitted through the two interfaces is a function of the refractive indices of the substances in the two cells. Thus, measurement of the transmitted light may be used to derive the refractive index of the substance in the detection cell, provided the refractive index of the material in the reference cell is known.

The deflection type of detector described above is less susceptible to changes in solvent composition than is the reflection type of detector. On the other hand, the deflection type of detector offers a smaller linear range than does the reflection type. Thus, prior art detectors have not fully combined the advantages of the reflection and deflection detectors.

Both of these principal refractive index detectors are adversely affected by changes in temperature of the liquid passing through their flow cells. This is because the refractive index of most liquids is dependent to some degree upon temperature. Therefore, measures must be taken to provide for temperature compensation of these devices. This technique adds to the complexity and expense of the detection instrument.

Various types of flow meters have been proposed for measuring flow rate of a fluid through a passage. Flow meter proposals typically require a member physically disposed in the fluid and linked to a measurement device. Oftentimes such a member is not conveniently combined with the system in question whose fluid flow rate is unknown.

Summary of the Invention

This invention provides method and apparatus for governing the fraction of light input to a flow cell which passes entirely through that cell as a function of the refractive index and flow rate of fluid within the cell.

An elongated flow cell is provided, with side walls, and entrance and exit windows in its ends. A fluid delivery system connected to the flow cell establishes a flow of fluid through the cell. A light directs divergent rays through the entrance window toward the exit window. A sensor produces a signal which is a function of the amount of light passing through the exit window.

In one embodiment, heat transmission apparatus is proximate to the flow cell and establishes a temperature gradient through the side walls of the cell. The temperature gradient has a component perpendicular to the longitudinal walls extending toward the middle of the flow cell. The fluid in the flow cell decreases in temperature and increases in refractive index with distance from the side walls. This causes the divergent rays entering the flow cell to bend away from the side walls. This bending makes the fraction of entering light which emerges from the exit window a highly dependent function of variations of the refractive index of the fluid in the flow cell for a given flow rate; conversely it provides a measure of flow rate if the refractive index of the effluent is known.

The flow cell has a generally elongated configuration, with an entrance window in one end and an exit window in the other, both of which are transparent to the passage of light. The light source is outside the entrance window and directs light through the cell and toward the exit window. In one embodiment, the light source provides a plurality of divergent light rays. The flow cell has input and output conduits connected to opposite ends. The input conduit is connected to receive the effluent from a liquid chromatograph column, in order to establish a flow of the effluent liquid through the cell.

The heat transmission apparatus is provided adjacent the longitudinal walls of the elongated flow cell. The heat transmission apparatus is controlled to establish and maintain a temperature gradient having a component across the longitudinal walls of the flow cell perpendicular to these walls. The component of the temperature gradient perpendicular to the walls extends inwardly toward the center of the flow cell in the preferred embodiment. The heat transmission apparatus may be a temperature controlled liquid bath into which at least a portion of the flow cell is submerged. A water jacket may also be provided surrounding the flow cell. Such heating apparatus for establishing a longitudinal gradient along the cell may also be utilized in the rate detecting embodiment according to another aspect of the invention.

These structures establish a temperature gradient within the liquid in the flow cell such that the liquid near the walls approaches the temperature of the heat transmission means, and declines with increasing distance inwardly from the longitudinal walls of the flow cell.

If the flow cell has a longitudinal dimension significantly larger than the dimensions of its cross-section, the amount of light which successfully passes through the flow cell is highly dependent on the temperature gradient established in the liquid of the flow cell and on variations in the refractive index of that liquid. The temperature gradient is influenced both by magnitude and geometry of the heat source, and by fluid flow rate. Over a significant range, as more bending of the divergent light rays takes place, and these rays are directed away from the walls, less of the energy of the light entering the entrance window is absorbed by incidence on the longitudinal walls of the flow cell and consequently more light passes out the exit window.

With respect to the refractive index indicator embodiment, the refractive index of any liquid is an increasing function of the density of that liquid. The density is, for most liquids, a decreasing function of its temperature. Light passing through a substance having an index of refraction which varies with position is refracted toward the denser areas. Therefore, in this aspect of the present invention, the divergent light rays directed incident to the walls of the flow cell tend to be bent away from the region of the walls, and toward the denser, cooler fluid in the central regions of the flow cell.

Therefore, if the temperature gradient is maintained at a substantially constant level with respect to a known flow rate, the amount of light passing through the cell will be a highly dependent function of the index of refraction of the liquid in the cell, over a substantial range of refraction index values.

Applicant has additionally discovered that the relationship between the fraction of input light emerging from the cell and the index of refraction of the fluid therein is substantially linear over a considerable range of refractive indices, that range encompassing the range of indices of refraction of practically all liquids which are useful in liquid chromatography applications.

An object of this invention is to provide a new and improved refractive index detector for use in a liquid chromatograph which renders the fraction of input light passing through a flow cell a function of the refractive index of the fluid within the flow cell.

With respect to the flow rate indicating embodiment of this invention, if the refractive index of the effluent is known, the amount of transmitted light through the cell is indicative of the flow rate of the fluid. By knowing boundary conditions of the specific cell and heat transmitting device utilized, measurement of absorbance of the fluid is indicative of its flow rate. Accordingly, another object of this invention is to provide a novel flow rate indicator and method used in a flow cell by determining the absorbance of a light beam directed therethrough.

Other objects of this invention will become apparent from the following detailed description, taken with the accompanying drawings.

DESCRIPTION OF THE PREFERRED EMBODIMENT

Figures 1, 1A:
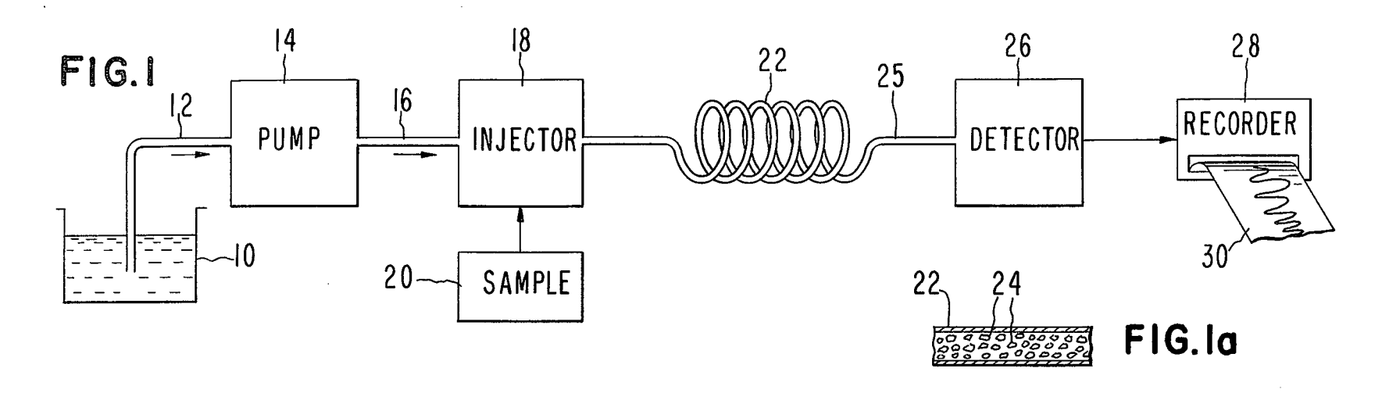
FIG. 1 is a block drawing of a liquid chromatographic system.
FIG. 1a is a detailed drawing of a segment of the column of the liquid chromatograph.

FIG. 1 shows a typical liquid chromatograph system to which one aspect of the present invention is applicable. A solvent reservoir 10 contains a quantity of solvent, which is drawn along a conduit 12 by a pump 14, and subsequently transported through a conduit 16 to an injector 18. A quantity of sample from a sample reservoir 20 is injected into the solvent by an injector 18. The solvent/sample solution continues on to a column 22. The column 22 is an elongated conduit containing a stationary phase 24 which is shown in FIG. 1a as a solid particulate material.

Components of the sample are selectively retained in the column 22 by the stationary phase 24, emerging in the column effluent at an end 25 of the column 22 in particular time-related patterns. The presence and concentration of these components in the effluent are sensed by a detector 26. The detector 26 generates a signal as a function of the concentration of the component detected, which signal is directed to a recorder 28. The recorder 28 produces a tangible record 30 of the detected concentration of the sample components with respect to time.

Figures 2, 3:
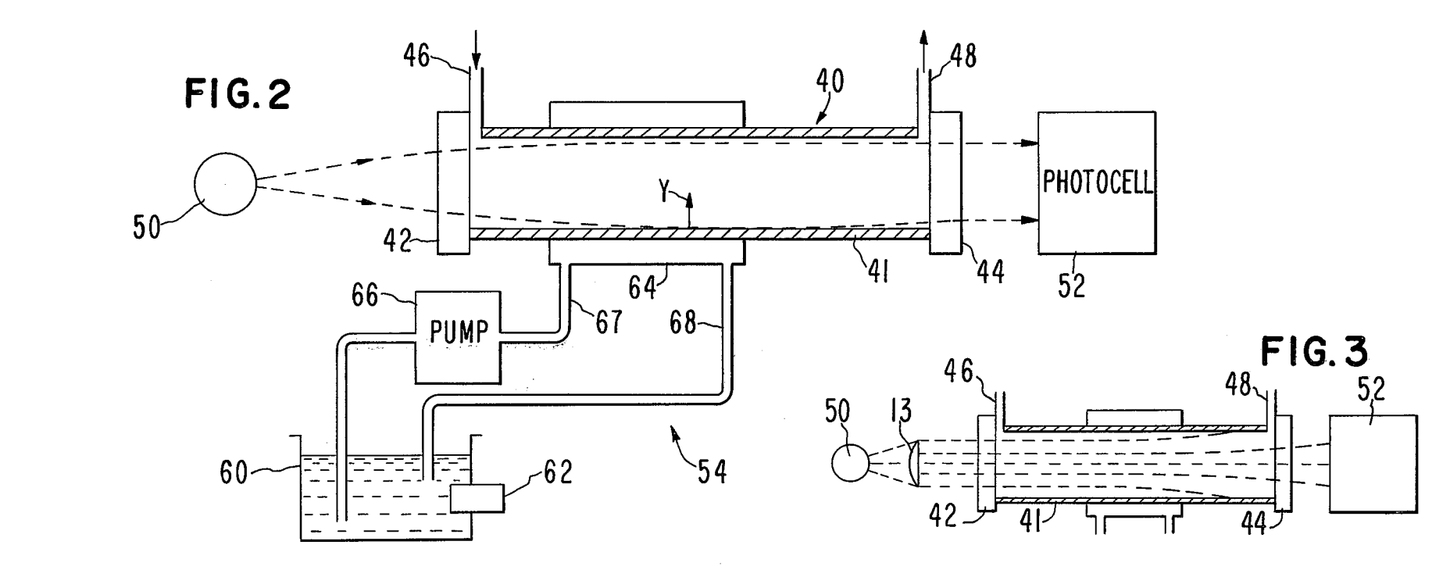
FIG. 2 is a side sectional view of apparatus used in this invention of one preferred form.
FIG. 3 is a side sectional view of apparatus according to this invention, showing an alternate embodiment incorporating parallel light rays, and a negative temperature gradient across the walls of the flow cell.

Referring to FIG. 2, a detector apparatus embodying the present invention is shown in detail. An elongated flow cell 40 is provided, having side walls 41, and an entrance and an exit window 42 and 44 respectively, located in opposite ends of the flow cell 40. An inlet conduit 46 is connected to and delivers effluent from the chromatorgraphic column 22 to the flow cell 40, through which the effluent circulates before exiting by way of the outlet conduit 48, for collection or discard. A light 50 directs divergent rays through the entrance window 42 toward the exit window 44. A photocell 52 senses the amount of light emerging from the exit window 44.

A heat transmission apparatus 54 provides a temperature gradient $dT/dy$ across the side walls 41 of the cell 40, extending toward the center of the cell. Temperature gradient $dT/dy$ is defined as the rate of change of temperature, T, with respect to displacement along a direction indicated as $y$ in FIG. 2. The temperature gradient causes the divergent rays entering the flow cell 40 to bend toward the center, away from the warmer fluid near the side walls 41. This bending increases the amount of light which passes through the flow cell 40 and renders the function of input light emerging through the cell a highly dependent function of variations in the refractive index of fluid within the flow cell.

The side walls 41 of flow cell 40 are heat transmissive. The cross-sectional configuration of the flow cell 40 is optimally circular, but may be such other shape as may be determinable as useful by those skilled in the art. The entrance window 42 and the exit window 44 are transparent. The inlet conduit 46 and the outlet conduit 48 are connected to the cell, the inlet conduit 46 being preferably connected to the source of fluid effluent from the analysis column of a liquid chromatograph. The flow of liquid through the flow cell 40 is generally in the direction from the inlet conduit 46 to the outlet conduit 48.

The light 50 is provided such that it directs divergent light rays, shown by the arrows in FIG. 2, through the entrance window 42 and toward the exit window 44. The photocell 52 is positioned to receive the light emerging from the exit window 44, and to produce a signal which is a function of the amount of light so received.

The heat transmission apparatus 54 is positioned proximate to the longitudinal walls 41 of the flow cell 40. The heat transmission apparatus is located such that it establishes the temperature gradient $dT/dy$ across the walls of the flow cell 40, which temperature gradient has a component perpendicular to the walls and extending inwardly toward the central region of the flow cell 40. This perpendicular component of the temperature gradient need not be uniform along the entire length of the longitudinal walls 41, but should not be time-varying.

The heat transmission means 54 may suitably comprise a liquid reservoir 60 maintained at a predetermined temperature by a control system 62 devisable by one of skill in the art, the liquid of the reservoir 60 being exposed to at least a portion of the longitudinal walls 41 of the flow cell 40 by a water jacket 64 around the flow cell 40. Liquid from the bath 60 is circulated through the jacket 64 by a pump 66 and conduits 67 and 68.

The refractive index of most liquids is an increasing function of the density of that liquid. The density, in turn, is a decreasing function of its temperature. Light passing through a medium having an index of refraction which varies as a function of position tends to be refracted toward that portion of the medium having the higher refractive index. That is to say, light is refracted toward the denser (cooler) portions of the medium.

FIG. 2 shows how this phenomenon enables the operation of the detector of this invention. Because the temperature gradient extends inwardly from the walls toward the center of the flow cell 40, the fluid therein decreases in temperature with distance from the side walls. The warmer material is near the periphery, the cooler toward the center. FIG. 2 shows diverging light rays entering the flow cell 40 through the entrance window 42. According to the phenomena discussed above, these light rays tend to be bent toward the cooler or central portions of the flow cell. Rays which would otherwise strike the side walls 41, and either pass through them or be absorbed by them, are bent such that they proceed down the entire length of the flow cell and pass through the exit window 44, where they are sensed by the photocell 52.

If the temperature gradient $dT/dy$ is maintained constant with respect to time, the amount of the light from light source 50 which ultimately passes through the entire flow cell for a given flow rate becomes a function of variations of the refractive index of the fluid in the flow cell. Within a substantial range, the higher the refractive index, the more light is passed all the way through the flow cell, because more of the divergent rays are bent away from the side walls 41.

The mathematical basis specifying the relationship between the index of refraction of the fluid within the flow cell 40 and the amount of light emanating from light source 50 which exits through the exit window 44 is discussed below.

It can be shown that the amount of light transmitted through a narrow bore flow cell is representable by the following expression:

$$\frac{\Delta I}{I} = \frac{L^2}{s} \frac{1}{n} \frac{dn}{dT} \frac{dT}{dy} \quad (1)$$

where L is the cell pathlength, s is the cell radius, n is the refractive index of fluid in the cell, T is the temperature, and $dT/dy$ is the temperature gradient at the cell wall. I represents the amount of light emitted by the light source and entering the cell, and $\Delta I$ is the amount of light lost in passage through the cell.

The refractive index enters this expression as $$\frac{1}{n} \frac{dn}{dT} \quad (2)$$

This expression can be evaluated by use of the Lorenz-Lorentz relationship $$\frac{n^2 - 1}{n^2 + 2} = k\rho \quad (3)$$

where $k$ is a constant for a given fluid and $\rho$ is the density.

From equation (3)

$$\left[ \frac{2n}{n^2+2} - \frac{(n^2-1) 2n}{(n^2+2)^2} \right] dn = k\, d\rho$$

$$\frac{6n}{(n^2+2)^2} dn = k\, d\rho$$

$$\frac{1}{n} \frac{dn}{dT} = \frac{(n^2+2)^2}{6 n^2} k \frac{d\rho}{dT}.$$

But, $$-\frac{1}{\rho} \frac{d\rho}{dT} = \beta,$$

where $\beta$ is the thermal coefficient of expansion.
Thus, $$\frac{1}{n} \frac{dn}{dT} = - \frac{(n^2+2)^2}{6 n^2} k\rho\beta = -\frac{(n^2+2)^2}{6 n^2} k \frac{1}{k} \frac{(n^2-1)}{(n^2+2)}$$

$$\frac{1}{n} \frac{dn}{dT} = - \frac{(n^2+2)(n^2-1)}{6 n^2} \beta \quad (4)$$

$$\frac{\Delta I}{I} = C \frac{(n^2+2)(n^2-1)}{6 n^2} \quad (5)$$

where C is independent of refractive index.
Table I hereinbelow compares values of $$N = \frac{(n^2+2)(n^2-1)}{6 n^2}$$

with corresponding values of the linear expression $y = 0.6960n - 0.6553$.

This latter expression has been independently derived as one which very closely approximates the values of N as indicated in Table I.

TABLE I

| n | $n^2$ | $N = \frac{(n^2+2)(n^2-1)}{6 n^2}$ | $y = 0.6990n - 0.6553$ | percent deviation $100 \times \frac{(N-y)}{N}$ | |
|---|---|---|---|---|---|
| 1.00 | 1.000 | 0 | — | — | |
| 1.10 | 1.210 | .09285 | .1136 | −22.35 | |
| 1.20 | 1.440 | .17518 | .1835 | −4.75 | |
| 1.30 | 1.690 | .25109 | .2534 | −0.92 | |
| 1.31 | 1.7161 | .2585 | .2604 | −0.73 | |
| 1.32 | 1.7424 | .2657 | .2674 | −0.64 | |
| 1.33 | 1.7689 | .2730 | .2744 | −0.51 | (water) |
| 1.34 | 1.7956 | .2803 | .2814 | −0.39 | |
| 1.35 | 1.8225 | .2875 | .2884 | −0.31 | |
| 1.36 | 1.8496 | .2947 | .2953 | −0.20 | range of |
| 1.38 | 1.9044 | .3090 | .3093 | −0.10 | primary |
| 1.40 | 1.9600 | .3233 | .3233 | −0.00 | interest |
| 1.50 | 2.2500 | .3935 | .3932 | +0.08 | |
| 1.60 | 2.5600 | .4631 | .4631 | 0.00 | |
| 1.70 | 2.8900 | .5330 | .5330 | 0.00 | |
| 1.80 | 3.2400 | .6038 | .6029 | +0.15 | |
| 1.90 | 3.6100 | .6760 | .6728 | +0.47 | |
| 2.00 | 4.0000 | .7500 | .7427 | +0.97 | |
| 2.10 | 4.4100 | .8261 | .8126 | +1.63 | |

It can be seen from Table I that the values of these two expressions are equal to within 0.5 percent for the refractive index range of 1.33 to 1.9. This range of refractive indices includes practically all liquids of interest in liquid chromatography. The quartic/quadratic expression of refractive index in equation (5) can thus, for practical purposes, be closely approximated by a simple linear function. That is $$\Delta I/I = C (0.6990\, n - 0.6553) \quad (6)$$

If the solvent of the chromatographic column effluent has a refractive index of $n_1$ and the sample plus solvent has a refractive index of $n_2$, the change in light transmitted through the flow cell is proportional to $n_2 - n_1$. That is $$\Delta I_2 - \Delta I_1/I = 0.6990\, C\, (n_2 - n_1) \quad (7)$$

For small changes in sample concentration, the change in the refractive index of the sample plus the solvent fluids is essentially proportional to the sample concentration. Thus, the change in light transmitted through the flow cell is approximately proportional to the sample concentration in the column effluent.

Equation (7) shows that the sensitivity of the change in light passing through the flow cell is increased by increasing the quantity represented by the constant C. The magnitude of C is expressed as follows:

$$C = \frac{L^2}{s} \beta \frac{dT}{dy}. \quad (8)$$

The sensitivity of the refractive index detector of this invention is inversely proportional to the radius of the flow cell and directly proportional to the square of its length.

These parameters can be established by one of skill in the art in order to obtain the desired sensitivity for the detector. Applicant has found that one suitable embodiment of this invention incorporates a flow cell having a length of 10 centimeters, a radius of 0.025 centimeters, with a temperature drop along the cell wall of 10° C/cm and a volume flow rate of approximately 50 milliliters per hour.

Referring to FIG. 3, an alternate embodiment of this invention is shown. In this instance, the light source 50 emits light through the entrance window 42 which has been collimated into parallel rays by a collimator 13. The temperature gradient $dT/dy$ perpendicular to the side walls 41 of the flow cell in this embodiment extends outwardly from the cell walls, rather than inwardly. That is, the heat transmission apparatus removes heat from the longitudinal walls 41, such that the cooler regions of the fluid within the flow cell 40 lie near the walls, the warmer regions lying in the central areas.

As can be seen from FIG. 3, the parallel light rays entering the entrance window 42 tend to be bent outwardly toward the longitudinal walls of the cell 40. The degree of this bending, and the consequent reduction in the amount of light passing ultimately through the exit window 44 to the photocell 42, is a function of the refractive index of the fluid within the flow cell 40, provided that the temperature gradient $dT/dy$ remains constant with respect to time.

Thus, as in the previously described embodiment, the light emerging from the exit window 44 is a function of the refractive index of the liquid within flow cell 40 at a given flow rate.

The foregoing discussions have been generally directed towards determining refractive index of the fluid in the flow cell when flow rate is known. The flow rate indicator embodiment of the invention is next described wherein the refractive index value is known.

Combining equation (8) with equation (5) results in the equation.

$$\frac{\Delta I}{I} = \frac{L^2}{s} \beta \frac{dT}{dy} \frac{(n^2+2)(n^2-1)}{6n^2} \tag{9}$$

where $\Delta I/I$ represents the relative increase in light transmitted through the flow cell; and $\beta$ is the thermal coefficient of expansion. The partial derivative $\delta T/\delta y$ depends on the cell configuration and the mechanism which generates the temperature gradient normal to the cell wall. A uniform wall temperature requires a different expression for $\delta T/\delta y$ than does a linear wall temperature variation. Whether or not the fluid enters the cell at the wall temperature also greatly influences the form of the expression for $\delta T/\delta y$. $\delta T/\delta y$ is next calculated for several specific cell configurations.

Case 1

Uniform Wall Temperature With Fluid Entering Cell At Different Temperature.

Cholette reviewed experimental data and arrived at the following empirical expressions for heat transfer in laminar flow in a tube (M. Jakob, "Heat Transfer", vol. 1, p. 546, John Wiley & Sons, 1949).

$$N_{Nu_a} = C(N_{Gz})^n \text{ for } 10.5 < L/d < 63$$

and $$C = 2/\pi, n = 1 \text{ for } N_{Gz} < 5$$

$$C = 1.56, n = 0.4 \text{ for } N_{Gz} \text{ between 5 and 150}$$

where $$N_{Nu_a} = h_a d/k_a$$

(Nusselt Number evaluated at the arithmetic mean temperature of the fluid)

$$N_{Gz} = c_p \dot{m}/kL$$

(Graetz Number)

$h_a$ = film heat transfer coefficient
$d$ = diameter of tube, $L$ = length of tube
$k_a$ = thermal conductivity of fluid
$\dot{m}$ = mass flow rate of the fluid, $c_p$ = heat capacity It may be shown that the following single function does a reasonable job of approximating Graetz Numbers up to 25.

$$N_{Nu_a} = 5.62(1 - e^{-0.125 N_{Gz}}) \text{ for } N_{Gz} < 25 \tag{10}$$

The largest relative deviation of this single function from the dual function expression of Cholette occurs in the region of transition from one of Cholette's functions to the other. This transistion region extends from about $N_{Gz} = 3$ to $N_{Gz} = 7$.

$$h_a(T_a - T_w) = k\left(\frac{\delta T}{\delta y}\right)_w \text{ and } N_{Nu_a} = \frac{h_a d}{k_a} \tag{11}$$

$$\left(\frac{\delta T}{\delta y}\right)_w = \frac{1}{d} N_{Nu_a}(T_a - T_w)$$

$$\left(\frac{\delta T}{\delta y}\right)_w = \frac{5.62(T_a - T_w)}{d}(1 - e^{-0.125 N_{Gz}})$$

for $N_{Gz} = \frac{c_p \dot{m}}{kL} < 25$ and $10.5 < L/d < 63$

Combining equations 9, 10 and 11 to form equation 12, $$\frac{\Delta I}{I} = -\frac{L^2}{s} \frac{(n^2+2)(n^2-1)}{6n^2} \beta \frac{5.62}{d}(T_a - T_w)\left(1 - e^{-0.125\left(\frac{\rho c_p}{kL}\dot{V}\right)}\right) \tag{12}$$

where $$\frac{\rho c_p}{kL}\dot{V}$$

is substituted for $N_{Gz}$.

The volume flow rate, $\dot{V}$, only appears in the exponent. Equation (12) can therefore be written:

$$\Delta I/I = C_1 (1 - e^{-C_2 \dot{V}})$$

where $C_1$ & $C_2$ are independent of flow rate. Rearranging terms, $$1 - \frac{1}{C_1} \frac{\Delta I}{I} = e^{-C_2 \dot{V}}$$

From the Binomial Theorem, $(1 - x)^n = 1 - nx + \ldots$ $$1 - \frac{1}{C_1} \frac{\Delta I}{I} \doteq (1 - \frac{\Delta I}{I})^{\frac{1}{C_1}} \text{ for } \frac{1}{C_1} \frac{\Delta I}{I} \ll 1$$

$$(1 - \frac{\Delta I}{I})^{\frac{1}{C_1}} \doteq e^{-C_2 \dot{V}}$$

Taking natural logarithms of both sides, $$\frac{1}{C_1} \ln (1 - \frac{\Delta I}{I}) = -C_2 \dot{V}$$

$$\dot{V} = -\frac{1}{C_1 C_2} \ln (1 - \frac{\Delta I}{I}) \quad (13)$$

Definition of Absorbance:

$$\text{Abs.} = -\log I/I_o = -\log (\frac{I - \Delta I}{I})$$

$$\text{Abs.} = -\frac{1}{2.303} \ln (1 - \frac{\Delta I}{I})$$

$$\dot{V} = -\frac{1}{C_3} \ln (1 - \frac{\Delta I}{I})$$

$$\text{Absorbance} = -\frac{1}{C_4} \ln (1 - \frac{\Delta I}{I}) \quad (14)$$

The volume flow rate is related in the same way as absorbance to change in eight intensity transmitted through the flow cell for the special case under consideration. Contemporary electronics developed to give outputs linear with absorbance can be readily modified using ordinary skill in combination with this teaching to give a signal which is proportional to flow rate in the above described embodiment.

SPECIFIC EXAMPLE FOR UNIFORM WALL TEMPERATURE CELL

Next described is a cell having a uniform wall temperature with the following parameters:

$L = 10$ cm, $s = 1.0$ mm, Fluid = Isooctane (2,2,4 trimethylpentane 0.01 change in absorbance corresponds to flow rate change of 0 to 100 ml/hr.

$$\text{absorbance} = -\log_{10} I/I_o = -(1/2.303) \ln I/I_o$$

$$dA = -\frac{1}{2.303} \frac{I_o}{I} \frac{d(I)}{I_o}$$

but $I_o/I \doteq 1.0$ so $\Delta I/I = -2.303 A = 2.303 \times 10^{-2}$ at $\dot{V} = 100$ ml/hr $N_{Gz} = 813 (\dot{V}/L) = 2.26$ $1 - e^{-0.125 \times 2.26} = 1 - e^{-0.282} = 1 - 0.75 = 0.25$ $$n = 1.39, \quad \frac{(n^2+2)(n^2-1)}{6 n^2} = \frac{3.93 \times 0.93}{6 \times 1.93} = 0.316$$

$$= 10.24 \times 10^{-4}$$

Substituting above in equation (12)

$2.303 - 10^3 (0.316) (10.24 \times 10^{-4}) (5.62/0.2) (0.25) (T_a - T_w)$ $(T_a - T_w) = 0.0101$ °C error in equation (14) due to binominal expansion:

$$\text{next term} = \frac{\frac{1}{C_1} (\frac{1}{C_1} - 1) (\frac{\Delta I}{I})^2}{2}$$

$$\frac{1}{C_1} \frac{\Delta I}{I} = 0.25, \quad \frac{1}{C_1} = \frac{0.25}{0.023} = 10.9 \text{ at } \dot{V} = 100 \text{ ml/hr}$$

so next term in binomial expansion $$= \frac{(10.9)(9.9)}{2} (2.3 \times 10^{-2})^2$$

$$= 0.0285$$

previous term in binomial expansion $$= \frac{1}{C_1} \frac{\Delta I}{I} = 0.25$$

$0.0285/0.25 = 0.11$ or $11\%$.

Since series is oscillating in sign, the error due to other terms not included in deriving equation (14) is less than 11% at 100 ml/hr for the specific example chosen.

CASE 2

Linear Temperature Change Along Cell Wall With Fluid Entering Cell At Temperature Of Wall Next described is a cell having a linear temperature change along the cell wall with the fluid entering the cell substantially at the temperature of the wall $$T = K \cdot x$$

where $K$ is a constant.

If frictional heating is neglected, the temperature distribution is described by following differential equation; Under steady state, $\delta T/\delta t = 0$.

Fully developed Poiseuille flow;

$$v = v_x = 2 v_m (1 - r^2/s^2)$$

where $v_m$ is the mean velocity of the fluid.

Because of the axial symmetry, each radial temperature profile will be the same as neighboring profiles. In other words, an equal amount of heat flows into the fluid per unit length along the entire cell. The axial and radial variables can be separated as follows;

$$T = Kx + f(r)$$

where $K$ is independent of $x$ and $f(r)$ is a function of $r$ only.

$$\vec{v} \cdot \text{grad } T = (v_x) \left( \frac{\delta T}{\delta x} \right) = 2 v_m (1 - r^2/s^2) K$$

$$\nabla^2 T = \underbrace{\frac{\delta^2 T}{\delta x^2}}_{= 0} + \frac{1}{r} \frac{\delta}{\delta r} \left( r \frac{\delta f}{\delta r} \right)$$

$$\frac{1}{r} \frac{\delta}{\delta r} \left( r \frac{\delta f}{\delta r} \right) = \frac{1}{\alpha} 2 v_m (1 - r^2/s^2) K$$

Integrating:

$$r \frac{\delta f}{\delta r} = \frac{2 v_m}{\alpha} \left( \frac{r^2}{2} - \frac{r^4}{4 s^2} + C \right) K$$

$$f = \frac{2 v_m K}{\alpha} \left( \frac{r^2}{4} - \frac{r^4}{16 s^2} + C \ln r + D \right)$$

Boundary Conditions; $f$ remains finite at $r = 0 \dashrightarrow C = 0$
$f = 0$ at $r = s \dashrightarrow D = - (3 s^2/16)$ $$f = - \frac{v_m K s^2}{2 \alpha} \left( \frac{3}{4} - \frac{r^2}{s^2} + \frac{1}{4} \frac{r^4}{s^4} \right)$$

$$\frac{\delta T}{\delta r} = \frac{\delta f}{\delta r} = - \frac{v_m K s^2}{2 \alpha} \left( - \frac{2r}{s^2} + \frac{r^3}{s^4} \right)$$

$$\left. \frac{\delta T}{\delta r} \right)_{r=s} = + \frac{v_m K s^2}{2 \alpha}$$

but since $$v_m = \frac{\dot{V}}{\pi s^2} \qquad \frac{\delta T}{\delta y} = \left. \frac{\delta T}{\delta r} \right|_{r=s} = \frac{\dot{V} K}{2 \pi \alpha} \qquad (15)$$

SPECIFIC EXAMPLE

Linear temperature profile along wall, 10 cm path length, 2 mm inside diameter flow cell with isooctane as fluid and 100 ml/hr corresponds to absorbance change of 0.01

Combination equations 9, 10 and 15 gives $$\frac{\Delta I}{I} = - \frac{L^2}{s} \frac{(n^2+2)(n^2-1)}{6n^2} \left( - \frac{\dot{V} K}{2 \pi \alpha} \right) = 2.303 \times 10^{-2}$$

$$K = \frac{2.303 \times 10^{-2}}{1.16} = 0.020 \, °C/cm = K$$

CASE 3

Uniform Wall Temperature With Fluid Entering Cell at Wall Temperature - Temperature Gradient at Wall Generated By Frictional Heating In Fluid.

Differential Equation Governing Heat Transfer $$\alpha \nabla^2 T = - \frac{\nu}{2 c_p} \left( \frac{\delta v_i}{\delta x_k} + \frac{\delta v_k}{\delta x_i} \right)^2 \quad \text{(Landau \& Lifshitz, "Fluid Dynamics", page 210)}$$

$$v = v_x = 2 v_m (1 - r^2/s^2)$$

$$\frac{\delta v_x}{\delta r} = - \frac{4 v_m r}{s^2}$$

$$\frac{1}{r} \frac{\delta}{\delta r} \left( r \frac{\delta T}{\delta r} \right) = - \frac{8 \nu v_m^2}{c_p \alpha s^4} r^2$$

Integrating, $$r \frac{\delta T}{\delta r} = - \frac{2 v_m^2 \nu}{\alpha c_p s^4} r^4 + B$$

$$T = - \frac{v_m^2 \nu}{2 \alpha c_p s^4} r^4 + B \ln r + C$$

Boundary Conditions, $T$ finite at $r = 0 \dashrightarrow B = 0$ $T = T_o$ at $r = s \dashrightarrow C = T_o + v_m^2 \nu / 2 \alpha c_p$ $$T - T_o = \frac{v_m^2 \nu}{2 \alpha c_p} (1 - r^4/s^4) \text{ but } \nu/\alpha = N_{Pr} \text{ (Prandtl Number)}$$

$$T - T_o = \frac{v_m^2 N_{Pr}}{2 c_p} (1 - r^4/s^4)$$

$$\frac{\delta T}{\delta r} = - \frac{2 v_m^2 N_{Pr}}{c_p} (r^3/s^4)$$

$$\left. \frac{\delta T}{\delta r} \right)_{r=s} = - \frac{4 v_m^2 N_{Pr}}{c_p d} ; d = 2s \qquad (16)$$

SPECIFIC EXAMPLE 10 cm path length, 2mm inside diameter flow cell, isooctane as fluid, uniform wall temperature with frictional heating of fluid as only means of generating temperature gradient at wall Combining equations 9, 10 and 16.

$$\frac{\Delta I}{I} = \frac{L^2}{s} \frac{(n^2+2)(n^2-1)}{6n^2} \left. \frac{dT}{dr} \right|_{r=s}$$

assume $\dot{V} = v_m s^2 = 100$ ml/hr $= 1/36$ ml/sec $\Delta I/I = 10^3 (0.316)(10.2 \times 10^{-4})(2.26 \times 10^{-3})$ $\Delta I/I = 7.3 \times 10^{-4}$ Change in Absorbance $= 7.3 \times 10^{-4}/2.303$ $= 3.2 \times 10^{-4}$ (absorbance change corresponding to change in flow rate from 0 to 100 ml/hr in 2 mm diameter, 10 cm long flow cell)

Referring now to FIGS. 4a–4d, there are depicted several embodiments of flow cells similar to that of FIG. 2 except for the specific heat transmitting device 54. Elements similar understood elements described with respect to FIG. 2 have like members, and descriptions thereof are not repeated in the following discussion. Also, the electronic circuits for driving the heat transmitting elements and determining absorbance, although not shown, are understood to be as described with respect to FIG. 2. It is unerstood that the flow indicating apparatus and method of this invention is not limited to flow cells used exclusively in chromatography systems, but has been described in such a system for convenience.

Figure 4A:
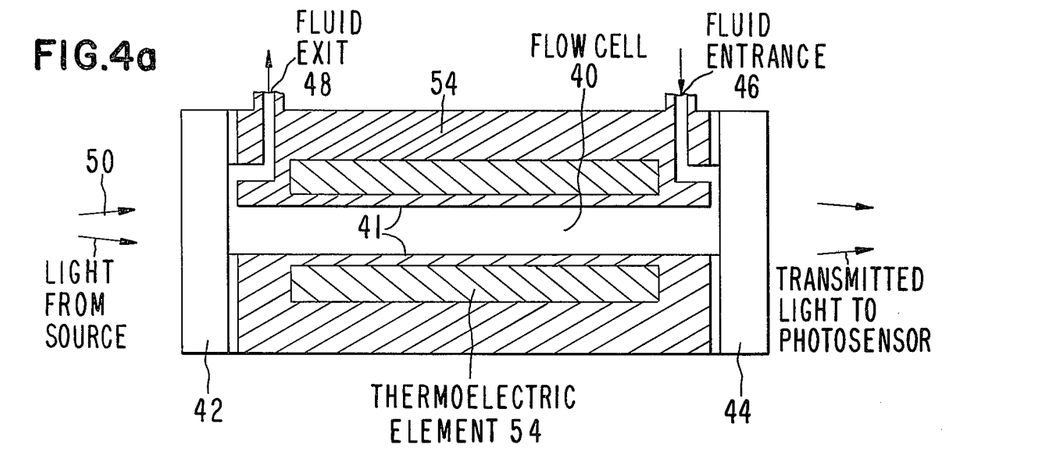
FIGS. 4a–4d illustrate fluid cells having various heat transmitting devices according to embodiments of the invention; and, FIGS. 5a and 5b illustrate heating generators maintaining the temperature of entering fluid at a fixed value relative to the cell wall temperature.

FIG. 4a illustrates a cell exhibiting a uniform wall temperature which generates a temperature gradient at the cell wall because the fluid enters the cell at a different temperature than the wall. The cell wall temperature is maintained by a thermoelectric element, replacing the water jacket of FIG. 2. Such apparatus as here depicted is suitably utilized in conjunction with the description of "Case 1" above.

Figure 4B:
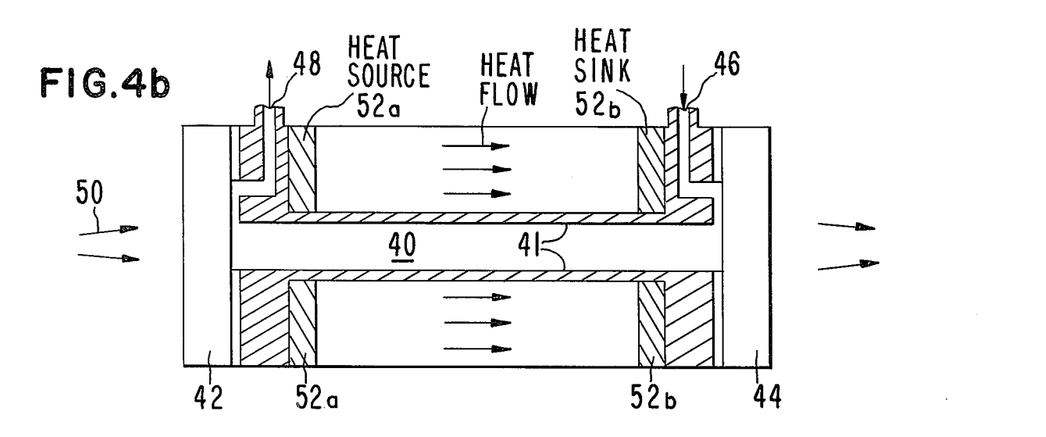

FIG. 4b depicts a flow cell having heat transmitting means comprising heat source 52a and heat sink 52b which establishes a wall temperature that varies as a linear function of distance along the cell. In this embodiment the fluid enters the flow cell at or near the temperature of the cell wall at the inlet end 46 of the flow cell. Heat flow into the fluid at the wall generates a temperature gradient in the fluid near the wall in a direction substantially transverse to fluid flow. A longitudinal flow of heat in the cell wall from heat source 52a to heat sink 52b generates a linear temperature profile along the cell. The heat source 52a is typically an electrical heater, which may be the light source lamp itself.

Figure 4C:
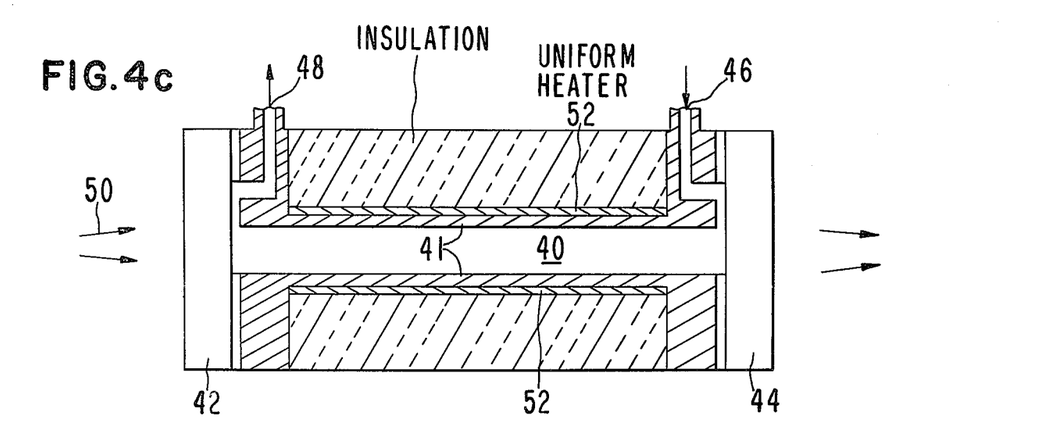

FIG. 4c depicts another embodiment of a flow cell having its wall temperature varying as a linear function of distance. Heater 52 uniformly surrounds flow cell 40 and has current flowing in a longitudinal direction along the cell walls 41. The uniform heater 52 may typically be of the resistive type. As the fluid enters the flow cell at or near the temperature of the cell wall at the inlet end, heat flows into the fluid creating a linear temperature profile along the cell wall. The flow cells depicted in FIGS. 4b and 4c are suitably utilized in conjunction with the above examples of "Case 2".

Figure 4D:
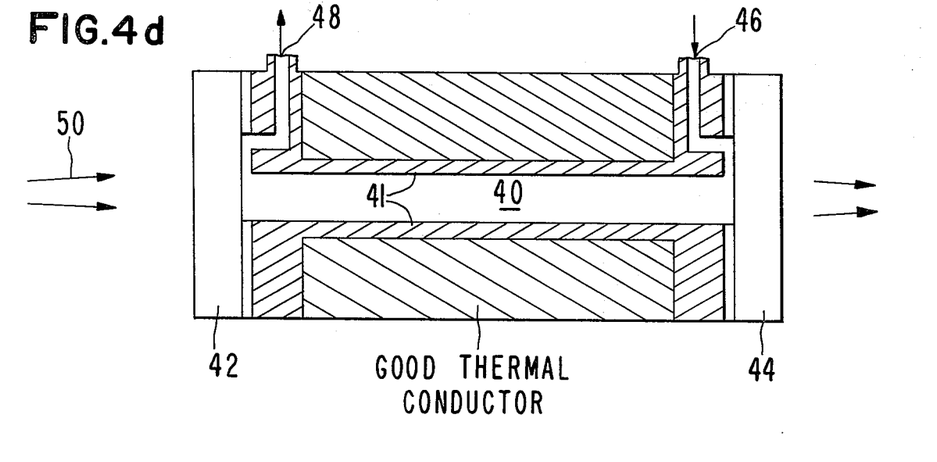

FIG. 4d illustrates a flow cell wherein the fluid enters the cell at the same temperature as the uniform wall temperature, and a gradient in temperature is generated at the wall by frictional heating of the fluid as it flows through the flow cell. That is, the above described heat transmitting apparatus is replaced by a thermal conductive jacket surrounding the wall 41 of the flow cell. Such a thermal conductor tends to prevent longitudinal gradients from developing within the cell. In some applications a stainless steel wall 41 provides adequate thermal conduction, and a thermal conducting jacket is unnecessary.

Figure 5A:
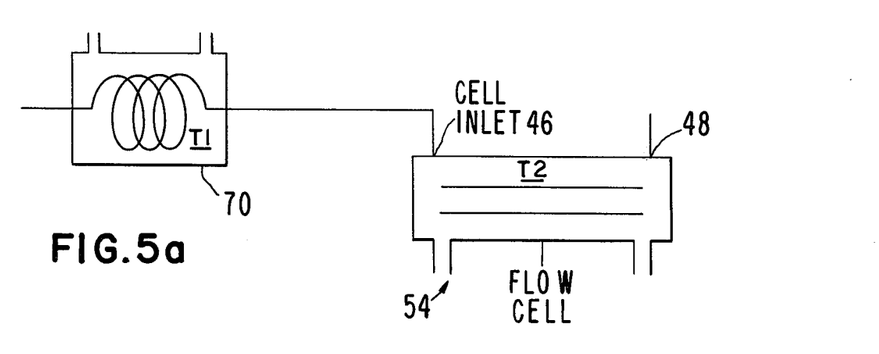
Figure 5B:
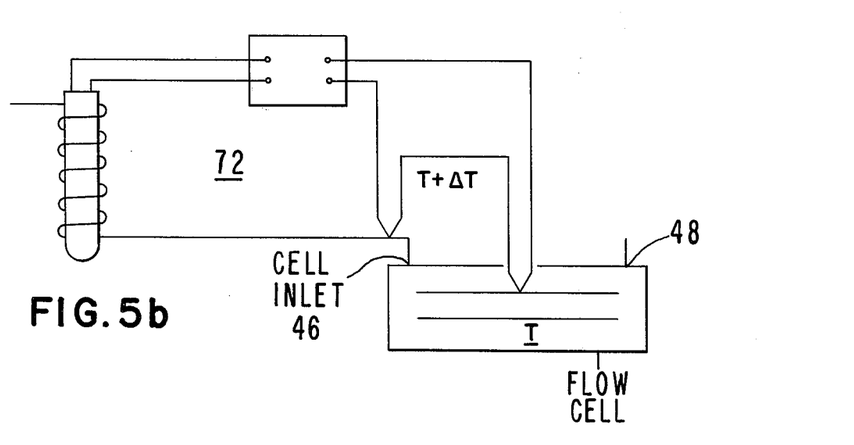

Referring now to FIGS. 5a and 5b, there are depicted flow cells having heating arrangements which control temperature of the incoming fluid. A separate thermoelectric element 70 preheats the incoming fluid to a desired absolute temperature T1 independent of the temperature T2 of the flow cell. A separate water jacket is also suitably utilized to preheat the incoming fluid.

Differential temperature sensing apparatus 72 maintains a temperature difference between the incoming fluid and the cell by way of a feedback circuit, which may utilize either a simple heating coil or a thermal-electric element. If the temperature of the cell wall is T degrees, than the incoming fluid is preheated and maintained at a temperature of $T + \Delta T$ for such applications as above described in "Case 1".

This invention provides a novel and effective apparatus and method for detecting the refractive index and flow rate of a fluid passing through a flow cell. Rather than compensating for temperature differentials in the fluid, applicant has devised a way of utilizing temperature differences in order to detect refractive index and flow rate.

The apparatus and method of this invention provide for almost perfect linearity of response over a wide range encompassing the indices of refraction of practically all liquids which are of substantial use in liquid chromatography.

The above described embodiments are intended to be illustrative, rather than exhaustive. Persons of ordinary skill in the art will be able to make certain modifications, alterations and changes in the embodiments based on this description, without departing from the spirit of this invention.

What is claimed is:
1. Apparatus for detecting rate of flow of effluent having a known index of refraction, said apparatus comprising:
   a. an elongated flow cell for passage of the effluent therethrough, said flow cell having light-transmissive oppositely facing light input and exit windows and thermally conductive side walls extending between said windows, passage of said fluid causing a temperature gradient to be generated at the walls of the cell by frictional heating;
   b. a light source for directing a beam of light through said input window along said thermally conductive side walls toward said exit window; and
   c. light sensing apparatus for generating a signal proportional to absorbance of the light passing through said exit window.

2. The apparatus for detecting rate of flow according to claim 1 and further including thermal conductive means contiguously surrounding said side walls.

3. Apparatus for detecting fluid rate of flow of effluent having a known index of refraction comprising:
   a. an elongated flow cell for passing the effluent having light transmissive, oppositely facing light input and exit windows and having side walls extending between said windows;
   b. a light source for directing light through said input window toward said exit window;
   c. heat transmission apparatus approximate to said sidewalls for maintaining a linear temperature gradient along said sidewalls and providing a temperature component perpendicular to and extending through said side walls; and,
   d. light sensing apparatus responsive to light passing through said window for producing a signal which is proportional to absorbance of the entering light.

4. The apparatus for detecting fluid rate of flow according to claim 3 wherein said heat transmission apparatus comprises a heat source adjacent one end of said flow cell and a heat sink adjacent the other end of said flow cell.

5. The apparatus according to claim 3 wherein said elongated flow cell comprises a circular cross section.

6. A method for detecting flow rate of a fluid comprising the steps of:
   a. passing the fluid through an elongated cell having side walls and input and exit windows in opposite ends thereof for permitting light to pass through the cell;
   b. maintaining a temperature gradient having a component perpendicular to and extending through said side walls for varying the index of refraction of the fluid as a function of distance from said sidewalls;

c. directing light through the input window towards the exit window; and, d. sensing the amount of light emerging from the exit window.

7. The method according to claim 6 further comprising the steps of measuring the light absorbance of said fluid from the sensed amount of light emerging from the exit window, and generating a signal indicative of said absorbance, said absorbance being substantially linearly related to fluid flow rate.

8. The method according to claim 7 wherein said step of maintaining said temperature gradient comprises maintaining said gradient extending longitudinally along the side walls of said cell, the fluid temperature thereby decreasing in magnitude in a direction inward from the side walls.

9. The method according to claim 7 wherein said step of disposing the fluid comprises the steps of preheating the fluid to a first temperature and passing the preheated fluid into the elongated cell.

10. The method according to claim 9 wherein said step of preheating includes the step of preheating the fluid to substantially the same temperature as the temperature of said sidewalls.

11. The method according to claim 9 wherein said step of preheating comprises the step of preheating the fluid to a first temperature different than the temperature of the sidewalls of said cell.

12. Apparatus for use in liquid chromatographic systems for detecting the refractive index of column effluent in the system, said apparatus comprising a. an elongated flow cell for containing the effluent and having light-transmissive light input and exit windows and side walls extending between said windows, b. a light source for directing light through said input window, c. light sensing means for producing a signal which is a function of the amount of light passing through said exit window, and d. heat transmission apparatus proximate to said side walls for maintaining a predetermined temperature gradient having a component perpendicular to and extending through said side walls and causing the density of the effluent in the cell to vary as a function of distance from said side walls, so that the refraction index of the effluent varies as a function of the distance from said side walls, and the amount of light passing through the cell and sensed by said light sensing apparatus is a function of said predetermined temperature gradient and of variations in the index of refraction of said effluent.

13. The apparatus of claim 12, wherein:
said elongated flow cell has inlet and outlet ports proximate to the ends thereof, said inlet port being connectable to the column of the liquid chromatographic system for maintaining a continuous flow of said effluent through said elongated flow cell.

14. The apparatus of claim 12, further comprising:
control means connected to said heat transmission apparatus for controlling said heat transmission means to maintain said temperature gradient at a constant level with respect to time.

15. The apparatus of claim 12, wherein:
a. said light source comprises a source of divergent light, and b. said temperature gradient extends in an inward direction through said side walls, so that said effluent decreases in temperature and its refractive index increases with respect to displacement toward the interior portion of said elongated flow cell, the effluent bending said divergent light toward the central region of the flow cell facilitating passage of the light through the flow cell as a function of variation in the refraction index of the effluent.

16. The apparatus of claim 12, wherein:
a. said light source comprises a source of parallel light rays, and b. said first temperature gradient extends outwardly through said side walls, so that said effluent increases in temperature with displacement toward the interior of said elongated flow cell, thus bending said parallel rays outwardly for absorption by the side walls as a function of variations in the refraction index of the effluent.

17. The apparatus of claim 12, wherein:
said inlet and exit windows are transparent.

18. The apparatus of claim 12, wherein:
said predetermined temperature gradient is uniform over the length of said side walls of said flow cell.

19. The apparatus of claim 12, wherein:
said heat transmission apparatus comprises:
a liquid bath maintained at a predetermined temperature, at least a portion of the side wall of said cell being exposed to the contents of said bath.

20. The apparatus of claim 12, wherein:
said elongated flow cell possesses a circular cross-section.

21. In a refractive index detector for use in a liquid chromatograph, said detector having an elongated flow cell including light transmissive oppositely facing light input and exit windows connected by side walls extending therebetween, a light source for directing light through the input window toward the exit window, and light detection means for sensing the amount of light from the light source emerging from the exit window and producing a signal which is a function of said amount of light, the flow cell being connectable to the outlet of an analysis column of a liquid chromatograph for continuous flow of the effluent therefrom through the flow cell, the improvement comprising:

a. heat transmission apparatus located proximate to the side walls of the flow cell for establishing a non-time varying predetermined temperature gradient having a component perpendicular to and extending through said side wall and causing the density of the effluent in the cell to vary as a function of distance from said side walls.

22. The improvement of claim 21, wherein:
a. said light source comprises a source of divergent light rays, and b. said temperature gradient extends in an inward direction through said side walls toward the central region of the flow cell, so that said effluent decreases in temperature and its refractive index increases with increasing displacement toward the interior portion of the flow cell, the effluent bending said divergent light rays toward the central region of the flow cell facilitating passage of the light through the cell as a function of variations in the refraction index of the effluent.

23. The improvement of claim 21, wherein:

a. said light source comprises a source of parallel light rays, and b. said temperature gradient extends outwardly through said side walls, so that said effluent increases in temperature with displacement toward the interior of said flow cell, thus bending said parallel rays outwardly to be absorbed by the longitudinal wall to a degree which is a function of variations in the refractive index of the effluent.

24. A method for detecting the refractive index of a fluid, said method comprising the steps of:

a. disposing the fluid in an elongated cell having side walls and an input and an exit window in opposite ends thereof for permitting light to pass through the cell, b. maintaining a predetermined temperature gradient having a component perpendicular to and extending through said side walls for causing the density of the fluid in the cell to vary as a function of distance from said side walls, c. directing light through the input window toward the exit window, and d. sensing the amount of light emerging from the exit window, causing the refractive index of the fluid to vary as a function of the distance from the side walls and the amount of light passing through the cell to be a function of variations in the index of refraction of the fluid.

25. The method of claim 24, wherein:

a. said light directing step comprises directing divergent light rays through said input window, and b. said step of maintaining said temperature gradient comprises maintaining said gradient extending in an inward direction through said side wall of said cell causing said fluid to decrease in temperature and its refractive index to increase with respect to displacement toward the interior portion of said elongated cell, the fluid bending said divergent light rays toward the central region of the cell facilitating passage of the light through the cell as a function of variations in the refractive index of the fluid at a predetermined temperature.

26. The method of claim 24, wherein:

a. said step of directing light comprises directing parallel light rays through said input window, and b. said gradient maintaining step comprises maintaining said first temperature gradient extending outwardly through said side walls, causing said fluid to increase in temperature toward the interior of said elongated cell, thus bending said parallel light rays outwardly for absorption by said longitudinal wall as a function of variations in the refractive index of the fluid.

27. The method of claim 24, wherein said step of maintaining a predetermined temperature gradient comprises:

a. maintaining a liquid bath at a predetermined temperature, b. directing at least a portion of the liquid in said liquid bath to contact the exterior of said side walls of the cell.

* * * * *